United States Patent [19]

Joshi

[11] Patent Number: 4,489,166

[45] Date of Patent: Dec. 18, 1984

[54] MONITORING OF HUMAN ENDOMETRIAL FUNCTION BY RADIOIMMUNOASSAY OF PEP

[75] Inventor: Sharad G. Joshi, Latham, N.Y.

[73] Assignee: Research Corporation, New York, N.Y.

[21] Appl. No.: 382,599

[22] Filed: May 27, 1982

[51] Int. Cl.³ ............................................ G01N 33/56
[52] U.S. Cl. .................................... 436/510; 436/539; 436/540; 436/542; 436/545; 436/804; 436/811; 436/814
[58] Field of Search ....................... 424/1, 1.1, 1.5, 85, 424/88, 177; 436/510, 536–540, 504, 542–545, 547, 65, 86, 804, 809, 808, 814, 817; 260/112 R

[56] References Cited

PUBLICATIONS

Chard, T., An Introduction to Radioimmunoassay & Related Techniques, Work, T. S. et al., eds. Elsevier Press (1976).
Joshi et al., J. Reproduct. Fertil., vol. 60, pp. 317–321, vol. 59, 273–285 (1980).
Joshi et al., Am. J. Obstet. Gynecol. vol. 138, p. 1131 (1980).
Sutcliffe, R. G. et al., J. Reprod. Fert. or Protides Biol. Fluids, vol. 24, p. 543 (1976).
Joshi, S. G. et al., Program, 10th Annual Meeting for the Society for the Study of Reproduction, Abst. 124 (1977).
Greenwood et al., Biochemical Journal, vol. 87, p. 14 (1963).
Joshi, S. G. et al., J. Reproductive Fertility, vol. 59, p. 287 (1980).
Joshi, S. G. et al., J. of Clinical Endocrinology & Metabolism, vol. 52 (6), pp. 1185–1192, (1981).
Greenwood, F. C., W. M. Hunter and J. S. Glover, "The Preparation of $^{131}I$-Labelled Human Growth Hormone of High Specific Radioactivity" Biochem. J. 89:114–123 (1963).
Sutcliffe, R. G. "The Search for New Human Fetal Proteins" Protides of the Biological Fluids 25, 543–546, 1976.
Mazurkiewicz, J. E. et al., "Immunocytochemical Localization of a Prosgestagen–Associated Endometrial Protein in the Human Decidua" J. Clin. Endocrin Metab., 52:1006–1008, 1981.
Joshi, S. G. et al., "Serum Levels of a Progestagen–Associated Endometrial Protein during the Menstrual Cycle and Pregnancy" J. Clin. Endocrin. Metab. 55:642–647.
Sutcliffe, R. G. et al., "Serological Identity between Human Alpha Uterine Protein and Human Progestagen Dependent Endometrial Protein" J. Reprod. Fert. 65:207–209 (1982).
Joshi, S. G. et al., "Pregnancy Associated Endometrial Protein in Women" In Cellular and Molecular Aspects of Implantation, 471–472 Plenum Press, New York.
Joshi, S. G. et al., "Radioimmunoassay for a Progestagen–Associated Protein of the Human Endometrium" Obstet. Gynecol. Surv. 36:635–637, 1981.
Joshi, S. G. et al., "A Progestagen–Associated Endometrial Protein (PEP) in the Sera of Non–Pregnant Women" Fertility and Sterility 37:307; 1982.
Joshi, S. G. et al., "Progestin–Dependent Proteins in the Human Endometrium" J. Steroid Biochem. 9:835, 1978.

Primary Examiner—Benjamin R. Padgett
Assistant Examiner—M. Moskowitz
Attorney, Agent, or Firm—Scully, Scott, Murphy & Presses

[57] ABSTRACT

The present invention relates to a novel method for the quantitative determination of PEP (progestagen-associated endometrial protein) in a body fluid by radioimmunoassay. The technique is useful in monitoring the function of the human endometrium.

37 Claims, 4 Drawing Figures

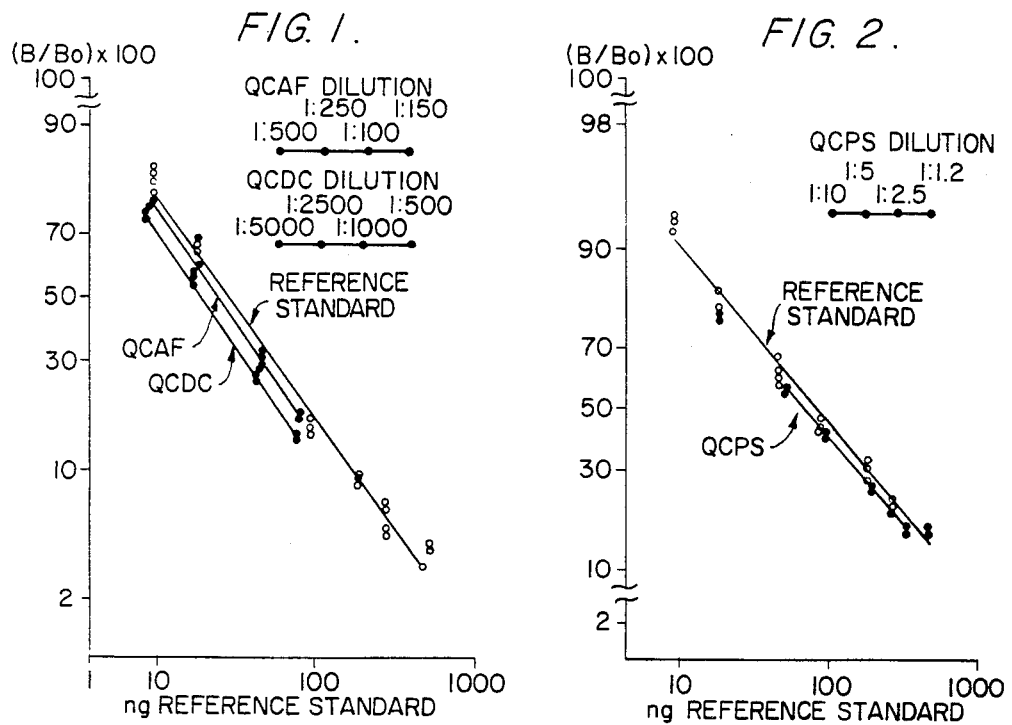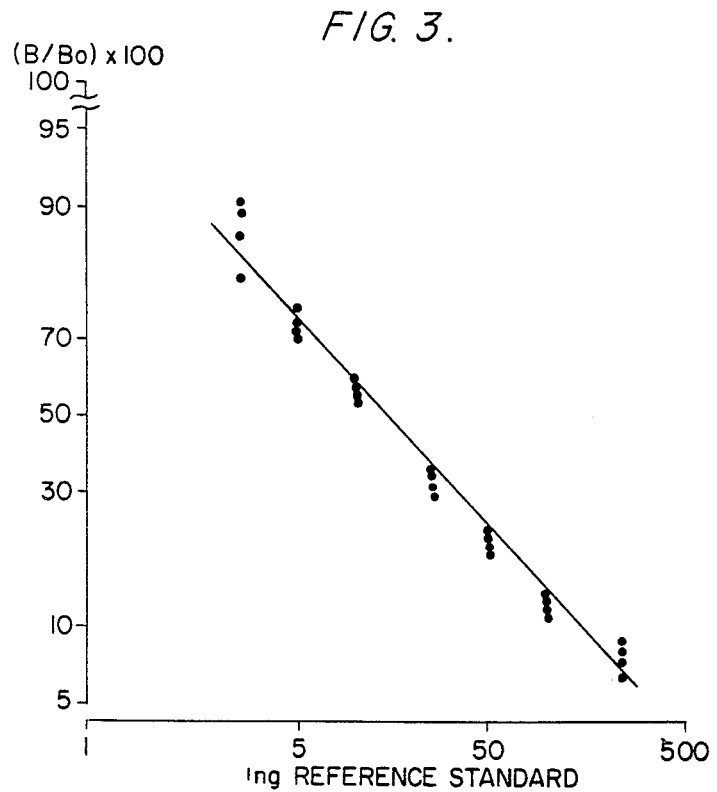

MONITORING OF HUMAN ENDOMETRIAL FUNCTION BY RADIOIMMUNOASSAY OF PEP

BACKGROUND OF THE INVENTION

Progesterone is the major secretory product of the corpus luteum (CL). Deficiency in either the duration or the amount of progestin secretion leads to an impairment of the endometrial development and its ability to support pregnancy. Progesterone and its synthetic analogues (progestins) are being widely used to restore the normalcy of the endometrium in a variety of clinical conditions including CL defects, habitual and threatened abortions, endometrial hyperplasias, and certain forms of endometrial cancers [Chez, R. A. *Fertil. Steril.*, Vol. 30, p. 16 (1978)]. They are also employed as contraceptive agents in a variety of delivery systems [Landgren, B. M., Lager, S., and Diczfalusy, E., *Contraception*, Vol. 23, p. 269 (1981); Somboonsuk, A., Israngkum, C., Siriwongse, T., Dusitin, N., Onthuam, Y., Chaudhary, R. R., Fuchs, F., Grossman, R., and Gray, R., *Contraception*, Vol. 18, p. 137 (1978); Newton, J., Szontagh, F., Lebech, P., and Rowe, P., *Contraception*, Vol. 19, p. 575 (1979); Toivonen, J., *Contraception*, Vol. 20, p. 511 (1979); Kurunmaki, H., Toivonen, J., Lahteenmaki, P. and Luukkainen, T., *Contraception*, Vol. 23, p. 473 (1981)]. In spite of such widespread use of progestins, very little is known about their biochemical effects on the human endometrium and the mechanisms by which these effects are produced. Moreover, the art lacks reliable means of monitoring the responses of endometrium in individual patients to endogenous or exogenous progestins.

Progesterone has been shown to bring about the differentiation of estrogen-dominated proliferative phase tissue into a secretory phase tissue. Continued stimulation of this target tissue with progesterone, as occurring in early pregnancy, promotes decidualization of the endometrial stromal cells and induces a hyper-secretory response within the glands. Studies on the mechanism of progestin action which have been conducted on animal models have clearly shown that progesterone, like many other steroid hormones, induces specific changes in the transcription and translation of the genetic messages encoded in the cellular DNA of the target cells [Glasser, S. R., Clark, J. H., Smith, R. G. and O'Malley, B. W. "Mechanism of Steroid Hormone Action in 'Endocrinology of Pregnancy'". Eds. F. Fuchs and Klopper, A. Harper and Row, New York (1977), pp. 15–40; Beier, H. M., *Biochim. Biophys. Acta.*, Vol. 160, p. 289 (1968); Squire, G. D., Bazer, F. W. and Murray, F. A., *Biol. Reprod.*, Vol. 7, p. 321 (1972); Laster. D. B., *Biol. Reprod.*, Vol. 16, p. 682 (1977)]. Specific progestin-dependent translation products such as uteroglobin, purple protein and an acidic protein, and a pregnancy-specific protein have been detected in the reproductive tract of laboratory animals by other investigators. However, such proteins are species-specific, and hence, of limited clinical utility.

Based on earlier evidence, we postulated that the action of progestin on the endometrium involves the preferential synthesis of a protein(s) which plays a key role in pregnancy. Analysis of the protein patterns of the progestin-dominated human endometrium led us to the detection of such a specific protein which we have designated "progestagen-associated endometrial protein", or PEP. The detection of such a PEP was first reported by us in May 1976 at the New York Academy of Science-sponsored Conference on Biochemical Actions of Progesterone and Progestins [Joshi, S. G. in Discussion (pp. 246–247) of the paper entitled "Protein Composition of Human Endometrium and its Secretion at Different Stages of Menstrual Cycle", by Hirsh, P. M., Fergusson, I. L. and King R. J. B., Ann. N.Y. Acad. Sci. Vol. 286, p. 233, (1977)]. A more detailed account of PEP was presented at the 10th Annual Meeting of the Society for the Study of Reproduction, held in 1977 in Austin, Tex., U.S.A. [Joshi, S. G., Ebert, K. M., and Swartz, D. P., Program of the 10th Annual Meeting for the Society for the Study of Reproduction, 1977. (Abstract No. 124)].

Our studies demonstrate that the endometrium is the major site of PEP synthesis and that PEP is formed within the endometrial glands and secreted into aminotic fluid and blood. We found that, in non-pregnant women, serum PEP levels reflect the stage of endometrial development, rather than the ovarian activity. In infertile women, induction of CL formation, but not stimulation of ovarian follicular activity, is associated with high serum PEP levels. IN normally cycling women, serum PEP levels increase markedly after ovulation reaching a peak during the late secretory phase. Synthesis of PEP is increased dramatically during early pregnancy (8–10 weeks) as indicated by more than 1000-fold and 10-fold increases in PEP levels in endometrial tissue and blood, respectively. Serum PEP level declines rapidly after about 14 weeks of pregnancy indicating the onset of degeneration of the endometrial glands.

Although the precise role of PEP in pregnancy has not been finally determined, the involvement of PEP in biochemical reactions that occur during implantation, invasion of the endometrium by trophoblasts and during immuno-suppression is being studied. Finally and, most importantly, our studies demonstrate that serum PEP represents a steroid-specific biochemical marker of the cumulative effect of progestins on the human endometrium. It is apparent, therefore, that serum PEP determination will prove to be a very valuable tool in the clinical practice: (i) to diagnose CL defects; (ii) to monitor the response of endometrium to endogenous or exogenous progestins in normal or abnormal pregnancies; and (iii) to predict response of endometrial hyperplasias or neoplasias to progestin therapy.

During our investigation, we developed several immunological methods for the detection of PEP. These included Ouchterlony's double diffusion test [Joshi, S. G., Ebert, K. M., and Swartz, D. P., *J. Reprod. Fert.*, Vol. 59, p. 273 (1980)], Scheidegger's micro immunoelectrophoresis [Joshi et al, supra], radioimmunoelectrophoresis [Joshi, S. G., Bank, J. F., and Szarowski, D. H., *J. Clin. Endocr. Metab.*, Vol. 52, p. 1185 (1981)], polyacrylamide gel electrophoresis combined with immunodiffusion [Joshi, S. G., Ebert, K. M., and Swartz, D. P., *J. Reprod. Fert.*, Vol. 59, p. 273 (1980)], and immunoperoxidase staining [Mazurkiewicz, J. E., Bank, J. F., and Joshi, S. G., *J. Clin. Endocr. Metab.*, Vol. 52, p. 1006 (1981)]. All of these tests utilized rabbit and goat antisera which were generated against partially purified proteins of the decidua (DE) of early pregnancy. Before use, such anti-PEP sera were thoroughly absorbed with human adult male serum and/or with cytosol of term placenta to remove contaminating antibodies [Joshi, S. G., Ebert, K. M., and Swartz, D. P., *J. Reprod. Fert.*, Vol. 59, p. 273 (1980); Joshi, S. G., Bank, J. F., and Szarowski, D. H., *J. Clin. Endocr. Metab.*, Vol, 52, p. 1185 (1981); Mazurkiewicz, J. E., Bank, J. F., and Joshi, S. G., *J. Clin. Endocr. Metab.*, Vol. 52, p. 1006 (1981)]. A preliminary screening of PEP in endometrial tissues in different developmental stages by immunodiffusion test and immunoelectrophoresis demonstrated the presence of PEP in all of forty-two specimens of DE (unavoidably contaminated with trophoblasts, fetal tissues and blood), in all of eight specimens of uncontaminated DE, in one decidua of tubal pregnancy, and in eighteen of thirty-eight samples of the proliferative phase endometria (PE) of cycling women, or in pregnancy or non-pregnancy sera [Joshi, S. G., Ebert, K. M., and Swartz, D. P. Program of the 10th Annual Meeting for the Society for the Study of Reproduction, 1977. (Abstract No. 124)].

A study [Joshi, S. G., Ebert, K. M., and Smith, R. A., *J. Reprod. Fert.*, Vol. 59, p. 287 (1980)] revealed that PEP is heterogeneous in several respects; in addition to being precipitated over a wide range of ammonium sulfate concentrations, it splits into different populations during chromatography on DEAE-cellulose or on hydroxypatite. Furthermore, during polyacrylamide gel electrophoresis and isoelectric focusing on acrylamide gels, PEP separates as a diffuse rather than a sharp band. PEP is a negatively charged protein with alpha mobility, and on acrylamide gels, it migrates in the post-albumin region. PEP is a glycoprotein which binds to Concanavalin-A. The immunologic reactivity of PEP is retained after 30-minute exposure to 4°–85° C. at pH 7.4 or after 2 hours to pH 2 to 11 at 22° C. Trypsin, but not pepsin, RNase, DNase or neuraminidase, completely destroys its immunoreactivity. The apparent molecular weight (MW), as determined by filtration on Sephadex G-100 or Sephacryl S-200 (Pharmacia), was found to be 47,000. PEP can be reductively dissociated into two subunits, each having MW of approximately 27,000. The isoelectric point determined by focusing on polyacrylamide gels was found to be approximately 4.9 Analysis of the cell fractions of DE homogenates obtained by the differential centrifugation method has shown the presence of PEP in the crude nuclei, heavy particulate fraction (15,000 xg, 20 minutes, sediment) and in cytosol but not in the light particulate fraction (130,000 xg, 90 minutes, sediment). Immunoperoxidase staining was employed to localize PEP in endometrial tissue, and it was found to be localized exclusively in glandular epithelial cells and within the glandular lumen.

An investigation was conducted to determine whether PEP is indeed synthesized within the endometrium, and if so, whether the rate of PEP synthesis is altered during the progestational phase development of the endometrium. This was determined by the conventional in vitro double-labeling technique. Briefly the technique involved labeling proteins of the endometrium in one developmental stage (e.g., proliferative phase) with $^{14}C$-leucine and proteins of the endometrium in another developmental stage (e.g., secretory or decidual phase) with $^{3}H$-leucine. After labeling, aliquots of soluble proteins derived from the endometria in the two developmental stages were combined and the mixtures (containing $^{14}C$- and $^{3}H$-labeled proteins) were treated with anti-PEP serum to precipitate PEP or they were electrophoresed on polyacrylamide gels in absence or presence of sodium dodecyl sulfate (native or SDS-gels). The results of the immunoprecipitation experiments showed that the ratios of $^{3}H/^{14}C$ (Exps. 1–4) or $^{14}C/^{3}H$ in the immunoprecipitates containing PEP were markedly higher than those in the original mixtures. The electrophoretic studies demonstrated that the ratios of $^{3}H/^{14}C$ in those segments of the acrylamide gels containing PEP were markedly higher than those in other segments of gels that did not contain PEP. It was concluded, therefore, that the rate of PEP synthesis is markedly higher in the secretory and in the decidual phase endometrial than in the proliferative phase endometria. In addition, electrophoretic studies on radio-proliferative endometrium also synthesized PEP but in amounts below the detection limit of immunodiffusion or immunoelectrophoresis.

It also became important to know whether the endometrium is the only or the major source of PEP in human females. Therefore studies were undertaken to study distribution of PEP in tissues and body fluids.

PEP could not be detected by immunoelectrophoresis or immunodiffusion in the pregnancy or non-pregnancy sera, the extracts of early-, mid- or full-term placentae, umbilical cord, and the extracts of ovaries, Fallopian tubes, myometria and cervixes that were dissected from the total abdominal hysterectomy specimens of women in proliferative secretory phase of menstrual cycle. Also PEP could not be detected in the extracts of kidney, liver and spleen or young women. However, PEP was readily detected by the relatively insensitive immunodiffusion technique in the secretory- and decidual-phase endometria of cycling and pregnant women and in the amniotic fluid samples obtained during 15–18 weeks of pregnancy [Joshi, S. G., Smith, R. A. and Stokes, D. K., *J. Reprod. Fert.*, Vol. 60, p. 317 (1980)]. We came to the realization that definite conclusions regarding the tissue-specificity of PEP could not be drawn unless more sensitive methods, such as a radioimmunoassay or an immunocytochemical technique, were developed for its detection in tissues or in specific cell types. Nevertheless, the studies conducted strongly suggest that the endometrium is the major, if not the sole, source of PEP in women.

Highly sensitive radioimmunologic tests demonstrate that PEP is *not* related to any of the following plasma, placental or uterine proteins: transferrin, α-1-anti-trypsin, ceruloplasmin, human prolactin, human chorionic gonadotropin, human placental lactogen, placental protein $SP_1$, pregnancy zone protein, human α-fetoprotein, pregancy-associated plasma protein (PAPP's) and uteroglobin. However, we have recently found that PEP is serologically identical to alpha-uterine protein (AUP) which was independently detected in amniotic fluid by Sutcliffe in 1976 [Sutcliffe, R. G., Joshi, S. G., Paterson, W. F. and Bank, J. F., communicated to J. Reprod. Fert. In Press; Sutcliffe, R. G., *Proteides Biol. Fluids*, Vol. 24, p. 543 (1976)]. However, the progestin-dependency of AUP was not studied by Sutcliffe.

The clinical applications of PEP depend heavily on the ability to detect and quantitate PEP in biological fluids and tissues which can be readily retrieved by relatively non-invasive means.

Heretofore there existed only one method for the quantitation of PEP in human tissues and body fluids, i.e., rocket immunoelectrophoresis (RIEP) (Joshi, S. G., Henriques, E. S., Smith, R. A., and Szarowski, D. H., Am. J. Obstet. Gynecol., 138, p. 1131 (1980), Sutcliffe, R. G., Brock, D. J. H., Nicholson, L. V. B. and Dunn, E. J., Reprod. Fertil. 54, p. 85 (1978).

It is an object of the present invention to provide radioimmunoassay methods for the detection of PEP in body fluids which are far more sensitive and vastly superior to the methods employed heretofore for the detection thereof.

It is a further object of the present invention to provide unlabeled PEP and a radioisotope labeled PEP useful in the above-noted radioimmunoassay methods.

It is a further object of the present invention to provide a method for the preparation of an antibody against PEP and a method for testing the quality thereof, said antibody also being useful in the above-noted radioimmunoassay method.

It is a further object of the present invention to provide a composition in kit form especially adapted for conducting the above-noted radioimmunoassay method.

It is a further object of the present invention to provide methods for diagnosing conditions of the human body which affect the production or maintenance of response of the endometrium to endogenous or exogenous progestins.

SUMMARY OF THE INVENTION

The invention relates to two different radioimmunoassay (RIA) methods, namely, "equilibrium-type" and "non-equilibrium-type" RIAs of PEP. Both comprise:
a. Admixing a sample of the body fluid suspected of containing PEP, radioisotope-labeled PEP, and an antibody produced in an animal against PEP (1st antibody),
b. incubating said mixture for a time sufficient to allow unlabeled PEP and radioisotope-labeled PEP to competitively bind to said 1st antibody,
c. separating from said mixture antibody to which is bound unlabeled PEP and radioisotope-labeled PEP, preferably by the addition of 2nd antibody which is produced in animal species different from that which is produced the 1st antibody and which is an antibody against the first animal species immunoglobulins and,
d. measuring the radioactivity of the separated antibody containing bound unlabeled PEP and radioisotope-labeled PEP.

The invention also includes PEP labeled with a radioisotope useful in the above-described radioimmunoassy method.

The invention also includes a method for preparing an antibody against PEP (1st antibody) prepared by immunizing an animal species with PEP and purifying the antibody against PEP from the serum of said animal.

The invention also includes the 2nd antibody against the above-described 1st antibody against PEP prepared by immunizing another animal species with the first animal species immunoglobulins.

The present invention also includes a composition in kit form adapted for the radioimmunoassay of a body fluid to determine the PEP content thereof comprising, in separate packages:
1. a radioisotope-labeled PEP
2. the 1st antibody against PEP, and optionally in separately packaged form, a 2nd antibody and a series of unlabeled PEP preparations to be used as reference standards The kit of the present invention also includes instructions for diagnosing conditions of the human body which affect the response of the human endometrium to endogenous or exogenous progestins.

The invention also includes the above-noted method of diagnosis, namely, determining the content of PEP in a body fluid rather than the tissues of a patient, preferably according to the above-described radioimmunossay method and ascertaining therefrom the level of endometrial response to progestins.

BRIEF DESCRIPTION OF THE DRAWINGS

FIG. 1 shows dose-response curves of PEP reference antigen in assay buffer, and dilutions of QCDC and QCAF in assay buffer.

FIG. 2 shows dose-response curves of PEP reference antigen in QCMS and dilutions of QCPS and QCMS.

FIG. 3 shows a dose-response curve of PEP reference antigen in assay buffer.

DETAILED DESCRIPTION OF THE INVENTION

Figure 4:
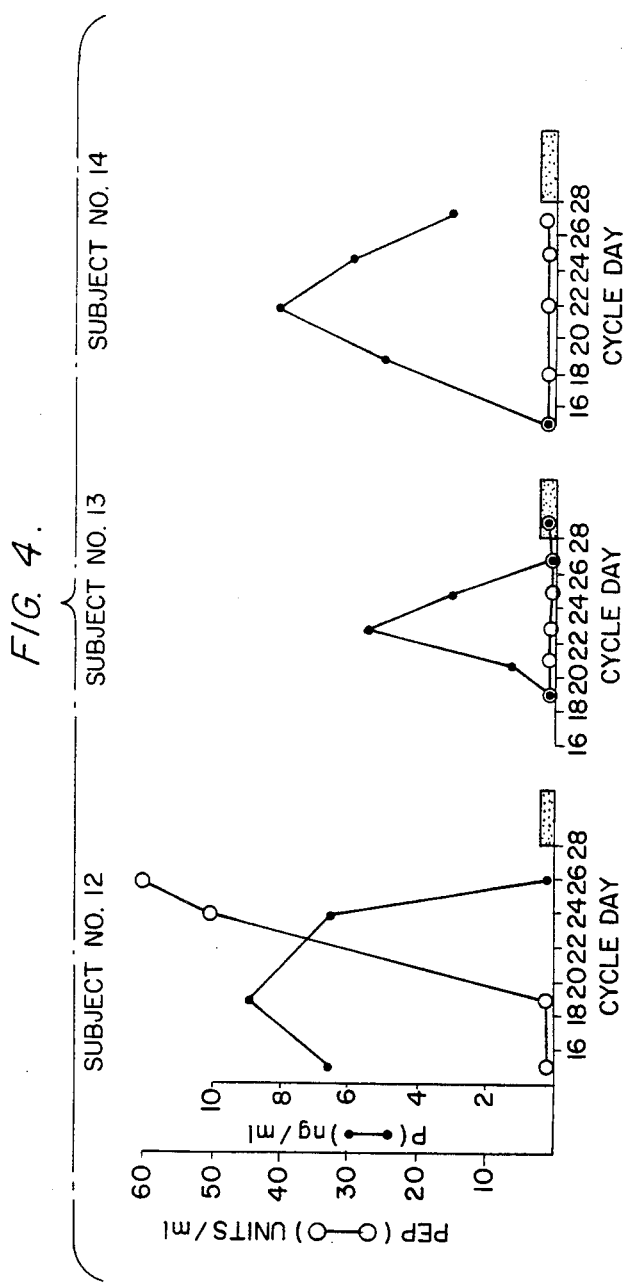
FIG. 4 shows patterns of changes in serum P(progesterone) and PEP (progestagen-associated endometrial protein).

Although the radioimmunoassay (RIA) method of the present invention is applicable for the detection and quantitation of PEP in any body fluid it is especially adapted for PEP determinations in serum, amniotic fluid, endometrial fluid, urine and tissue homogenizate.

The radiolabeled PEP may be prepared according to any conventional technique known for tagging a protein with such radioisotopes such as $^{125}I$, $^{131}I$, etc. Radiolabeling is achieved, for example, through the tyrosyl moiety of the protein by the conventional chloramine-T method of Greenwood et al, Biochem., J., 87: 114 (1963) and U.S. Pat. No. 4,260,737.

The anti-PEP antibody (the 1st antibody) is elicited from any suitable species of animal, e.g., goat, rabbit, etc.; however, it may also be produced by monoclonal antibody techniques.

In the radioimmunoassay methods of the present invention the antibody containing bound unlabeled PEP and radioisotope-labeled PEP is separated from the mixture by precipitation of the antibody-bound PEP and removal of the precipitate from the mixture.

The precipitation is preferably effected by inclusion in the mixture of the body fluid sample, unlabeled PEP and radioisotope-labeled PEP, the above-described 2nd antibody which is an antibody against said 1st antibody but is not an antibody against PEP. The second antibody forms a precipitate upon binding with the first antibody to which is bound unlabeled and labeled PEP.

The second antibody is derived from any suitable animal with the proviso that the animal be of a species different from that from which the first antibody was derived.

After measuring the radioactivity of the precipitate containing bound unlabeled and labeled PEP, the content of PEP in the original body fluid sample is determined by comparison of the measurement with a dose-response curve plotted from the results of the same RIA method applied to aqueous solutions containing known amounts of PEP.

The invention will be illustrated by the following non-limiting examples.

EXAMPLE 1

(Preparation of samples)

Paired samples of blood and endometria were obtained from 31 nonpregnant women, aged 20–45 years, who underwent dilation and curettage or hysterectomy for pelvic disease, or tubal ligation and dilation and curettage for sterilization. Also fourteen normally cycling subjects were selected from amongst a population of young women (aged 20-45 years) on the basis of a demonstrated biphasic basal body temperature (BBT) pattern during a pre-study cycle. These subjects were requested to refrain from using intra-uterine devices or steroidal forms of contraceptives and to maintain careful records of daily BBT and menstrual flow pattern during the study cycle. The day of the onset of the post-study cycle was arbitrarily designated as cycle day 28. During the study cycle, blood samples were drawn from each subject at two to three-day intervals beginning at day 16-19. Also, samples of blood were obtained from 53 pregnant women during pregnancy weeks 6-10, 15-28, or 29-40 and from several healthy men. In addition, single samples of blood were obtained from each of 201 women with normal, uncomplicated gestation who were enrolled in the study. These included patients of the full-time faculty of the Albany Medical College and the attending physicians at the Albany Medical Center Hospital, Albany, N.Y. Also, from two subjects, serial samples of blood were drawn at approximately weeky intervals during the 1st trimester of pregnancy (5-13 weeks). Gestational age was based on the last menstrual period. Samples of uterine decidua were obtained from 11 women who elected to terminate early pregnancy (6-10 weeks) by menstrual induction.

In addition, samples of amniotic fluid (AF) were procured during pregnancy weeks 14-18, 20-30, or 36-42 from 25 women who underwent amniocentesis for diagnosis of genetic disease of fetal maturity, or who elected to terminate midtrimester pregnancy by intraamniotic saline.

Routinely, a portion of each tissue from non-pregnant women was promptly fixed in buffered formalin and processed by standard procedures for histological examination. Based on such examinations, tissues were broadly classified as proliferative, early secretory, mid-secretory, or late secretory phase endometria, according to the guidelines described by Noyes et al, Fertil. Steril. 1: 3 (1950). The samples of non-pregnancy serum were also designated proliferative, early secretory, or midsecretory phase after histological classification of the donor endometria. Uterine decidua which were unavoidably contaminated with blood and fetal elements were processed to minimize the contaminants, according to the procedure described by Joshi et al, Reprod. Fertil. 59: 275 (1980). Tissue cytosols were prepared by homogenizing the tissues in RIA buffer (see below) and clarifying the tissue homogenates by high speed centrifugation (110,000×g, 90 min.) at 4° C. AF samples were also clarified by centrifugation (15,000×g, 15 min.) at 4° C. Pools of quality control decidual cytosol (QCDC) and quality control AF (QCAF) were obtained by combining aliquots of several decidual cytosols and AF which were obtained during pregnancy weeks 6-10 and 14-18, respectively. The blood samples were clotted and centrifuged at 4° C. to obtain sera. Samples of quality control male serum (QCMS) and quality control pregnancy serum (QCPS) were prepared by pooling several serum samples from men and from women in early pregnancy (6-10 weeks), respectively. All materials were stored at −10° C. until used.

Serum samples were also obtained from several other young cycling women and were pooled to generate control serum which is required to monitor the quality of RIAs of PEP and Progesterone (P).

EXAMPLE 2

(Preparation of antisera and antigens)

Antisera employed to study the specificity of binding of the tracer used in the RIA of PEP were: goat antiserum to uteroglobin [Beier, Biochim. Biophys. Acta., 160: 287 (1968)] (antiserum to day 5 pseudopregnant rabbit uterine fluid, supplied by the Baylor School of Medicine, Houston, TX); rabbit antisera to human transferrin, $\alpha$-antitrypsin, and ceruloplasmin (all from Behring Diagnostics, Woodbury N.Y.); rabbit antisera to human pregnancy-associated plasma proteins (PAPPs), PAPP-A, PAPP-C [Lin et al, Am. J. Obstet. Gynecol. 118: 223 (1974)] human pregnancy zone protein (hPZP) [Schoultz, Ibid, 119: 792 (1974)], and human placenta lactogen (hPL; all provided by the University of Miami School of Medicine, Miami, FL); rabbit antisera to human PRL (hPRL) and hCG (provided by NIAMDD and NICHHD, Bethesda, MD); rabbit antiserum to human placental protein [Bohn, Blut. 24: 292 (1972)] (supplied by Ohio State School of Medicine, Columbus, OH); and rabbit antiserum to human $\alpha$-fetoprotein [Joshi, J. Reprod. Fertil. 59; 287 (1970) (AFP provided by New York State Department of Health, Albany, NY).

A rabbit antiserum to partially purified PEP was prepared, as described by Joshi, supra, and used for quantitation of PEP in decidual protein fractions by rocket immunoelectrophoresis. A rabbit antiserum to a glycoprotein fraction of QCMS was used to detect glycoproteins of serum origin in PEP preparations. The serum glycoprotein fraction as the immunogen in rabbits was prepared by Concanavalin A-Sepharose chromatography, as described by Joshi, supra. Except for anti-hPRL and anti-hCG, which were not tested, the presence of precipitating antibodies in all of the antisera was confirmed by Ouchterlony's immunodiffusion test or by immunoelectrophoresis using appropriate antigen sources (purified antigens, placental extracts, uterine fluid, or pregnancy sera).

The following purified antigens were studied for their ability to compete with the binding of tracer PEP to anti-PEP in RIA; human transferrin and ceruplasmin, hCG (CR-119) and hPRL (both from the NIAMDD and NICHHD), and a concentrated preparation of rabbit uterine fluid (estimated to contain 20 mg uteroglobin/ml) from progesterone-treated animals (supplied by Case Western Reserve University School of Medicine, Cleveland, OH).

EXAMPLE 3

(Preparation of RIA reagents)

A double antibody RIA was set up using a partially purified decidual PEP as the source of reference standard, radioiodinated purified PEP as the tracer, goat anti-PEP as the first antibody, and rabbit antigoat immunoglobulin (IgG) as the second antibody. These reagents were prepared or procured as follows.

PEP was partially purified from the QCDC by a three-step procedure involving DEAE-cellulose chromatography, Concanavalin A-Sepharose chromatography, and gel filtration. The total amount of protein in the fractions obtained during PEP purification was estimated by Lowry's procedure [J. Biol. Chem. 193: 225 (1951)], and PEP was quantitated by rocket immunoelectrophoresis, as described by Joshi et al [Am. J. Obstet. Gynecol. 138: 1131 (1980)]. In DEAE-cellulose chromatography of QCDC, 10 ml of the packed exchanger (DE52, Whatman, Inc., Clifton, NJ), which was preequilibrated with the phosphate buffer (10 mM: pH 7.4) was mixed with the QCDC (200–250 mg protein in phosphate buffer) in a centrifuge tube, and the tube was agitated for 1 hour at 4° C. After centrifugation of the tube, the supernatant was aspirated and discarded, and the PEP which was bound to the exchanger was eluted with phosphate buffer supplemented with 100 mM NaCl. This PEP fraction was then subjected to Concanavalin A-Sepharose chromatography, as described by Joshi et al [J. Reprod. Fertil. 59: 275 (1980)], to obtain a glycoprotein fraction. The glycoprotein fraction was further fractionated by filtration on a column (1.5×90 cm) of Sephadex G-75 (Pharmacia Fine Chemicals, Piscataway, NJ) using the phosphate buffer containing 0.154 m NaCl as the eluting buffer. PEP-rich fractions were pooled, and aliquots of the partially purified PEP, designated PEP-1, were used for the production of an antiserum in a goat, as the reference standard in RIA, and for the preparation of the tracer for RIA.

Goat antiserum to PEP-1 was produced by the method of injecting the animal with the emulsion of antigen (PEP) in Freund's complete adjuvant at multiple subdermal sites. Booster injections of the antigen emulsion were given at 2-week intervals, and the animal was bled 1 week after each booster injection. The sera containing precipitating antibodies were pooled. Before use, the pooled goat antiserum was exhaustively absorbed with the QCMS by the procedure described by Joshi et al, Ibid, 59: 287, and an IgG fraction of the absorbed antiserum was prepared by the standard ammonium sulfate precipitation method. A portion of the IgG fraction (first antibody) containing 27 mg protein/ml phosphate buffer was saved for the IRA, the remaining material was coupled to CNBr-activated Sepharose-4B (Pharmacia) by the method of Knauf and Urbach [Amer. J. Obstet. Gynecol. 127: 705 (1971)] and the coupled product was used as an immunoabsorbent for further purification of PEP-1 by immunoaffinity chromatography.

To generate the tracer, PEP-1 was radioiodinated by the chloramine-T method of Greenwood et al, supra, before it was further purified by immunoaffinity chromatography. Routinely, 70 μg PEP-1 were radioiodinated for 30 sec. at 22° C. in the presence of 1 mCi [$^{125}$I] sodium iodide (iodine-125, protein iodination grade, high specific activity, New England Nuclear Corp., Boston, MA) and 50 μg chloramine-T in a final volume of 60 μl 0.05 M phosphate buffer, pH 7.2. The reaction was terminated by the addition of 100 μg sodium metabisulfite and 10 μg potassium iodide in 0.05 M phosphate buffer. Protein-bound iodine was separated from free iodide by gel filtration using a Sephadex G-75 column and 10 mM phosphate-0.5 M NaCl-0.1% (wt/vol) bovine serum albumin-0.1% (wt/vol) sodium azide, pH 7.4, as eluting buffer. The radioiodinated protein (SA, 12–16 μCi/μg) was then selectively absorbed on to the immunoabsorbent and eluted from the absorbent using experimental conditions identical to those described by Knauf and Urbach, supra. The purified [$^{125}$I] PEP (tracer) was dialyzed at 4° C. against RIA buffer [10 mM phosphate-0.154 M NaCl-50 mM EDTA-0.1% (wt/vol) bovine serum albumin-0.1% (wt/vol) sodium azide, pH 7.4] and stored in aliquots at −20° C. for up to 4 weeks before it was discarded.

Contaminating proteins in PEP-1 were detected by polyacrylamide gel electrophoresis in the presence of sodium dodecyl sulfate, immunoelectrophoresis, and Ouchterlony's immunodiffusion test, as described by Joshi et al [J. Reprod. Fertil. 59: 275 (1980)]. Radioimmunoelectrophoresis was carried out, as described by Prescott and David [Anal. Biochem. 57: 232 (1974)], to detect trace amounts of contaminating antigens in radioiodinated PEP-1 and PEP-2 preparations. Specificities of the antigen (PEP) and antibody preparations were investigated by double antibody RIA techniques as follows. The tracer ([$^{125}$I]PEP-2) was allowed to react with anti-PEP or specific antibodies to known pregnancy proteins (first antibodies) in the absence or presence of an excess of known pregnancy proteins (to study nonspecific binding). The antigen-antibody complexes were precipitated by the addition of an appropriate second antibody. In some studies, some of the known pregnancy proteins were allowed to compete for the binding of the tracer ([$^{125}$I]PEP-2) to anti-PEP.

EXAMPLE 4

(Analysis of the quality of the RIA reagents)

The reference antigen was obtained by a three-step procedure involving DEAE-cellulose, Concanavalin A-Sepharose, and Sephadex G-75 chromatographies which routinely provided 30- to 50-fold purification of PEP. However, the resultant product (PEP-1) was not homogenous. Polyacrylamide gel electrophoresis of the product in the presence of sodium dodecyl sulfate revealed one major protein band containing PEP and six other protein bands devoid of PEP. Five of the latter were of serum origin, and they were detected only by radioimmunoelectrophoresis of [$^{125}$I]PEP-1 using an antiserum to the glycoprotein fraction of QCMS. One of these five serum glycoproteins in PEP-1, three, namely, $\alpha_1$-antitrypsin, transferrin, and ceruloplasmin, were identified using monospecific antisera against serum proteins.

The tracer was prepared from [$^{125}$I]PEP-1 by immunoaffinity chromatography, as described above. In radioimmunoelectrophorectic studies, the tracer did not react with the antiserum to the glycoprotein fraction of male serum, but it reacted with the unabsorbed goat anti-PEP to form only one preciptin line. The acidic conditions (pH 2.5) which were used to elute PEP from the immunoabsorbent during immunoaffinity chromatography did not adversely influence the bindability of the antigen, since rechromatography of the tracer using the immunoabsorbent resulted in more or less complete reabsorption of the tracer onto the absorbent. Purified radioiodinated PEP bound readily to goat or rabbit anti-PEP, but it did not bind to antisera to several known pregnancy proteins, including uteroglobin, $SP_1$, AFP, hPL, PAPPs, PAPP-A, PAPP-C, hPZP, hCG, hPRL, transferrring, ceruloplasmin, and $\alpha_1$-antitrypsin when the antisera were used at 1:500 and 1:1000 final dilutions as sources of first antibodies in the double antibody RIAs.

As noted above, the first antibody required for the RIA of PEP was produced by immunizing a goat against PEP-1, followed by removal of the contaminating antibodies by absorption of the goat antiserum with QCMS and isolation of the Ig fraction of the absorbed antiserum. In the Ouchterlony immunodiffusion test, the Ig fraction of the absorbed goat antisera reacted only with cytosols of the uterine decidua and the midsecretory phase endometrium, but it did not react with the QCMS, QCPS, nonpregnancy serum, or cytosol of the prolferative phase endometrium. In radioimmunoelectrophoretic studies, the first antibody reacted with radioiodinated preparations of PEP-1 or PEP-2 to form only one preciptin line. In double antibody RIA studies, the diluted first antibody (100 μl of a 1:1250 dilution) reacted only with PEP and not with purified hCG (1 μg/tube), hPRL (1 μg/tube), 60$_1$-antitrypsin (1 mg/tube), or rabbit uterine fluid (containing 2-4 mg uteroglobin/tube).

EXAMPLE 5

(Equilibrium-type RIA of PEP)

For routine analysis of PEP in the cytosols of endometria from non-pregnant women and AF samples from pregnant women the reagents were added to 10×75 mm disposable glass tubes in the following order: RIA buffer in all tubes in a volume sufficient to adjust the final volume to 800 μl, 100-500 μl endometrial cytosol or 10-500 μl AF in tubes for unknowns, 100 μl RIA buffer containing 10-500 ng reference standard (PEP-1) in RIA buffer in tubes for the dose-response curve, 100 μl RIA buffer containing excess (3.5 μg) reference standard in tubes for the measurement of nonspecific binding (NSB) of the tracer for the first antibody (or trapping of the tracer during the precipitation of antigen-antibody complex), 100 μl first antibody solution (1:1250 dilution of the IgG fraction: 27 mg/ml, of the absorbed goat anti-PEP serum) in RIA buffer supplemented with 0.25% (wt/vol) normal goat serum, and 100 μl tracer solution (−40,000 cpm) in all tubes. When serum samples from pregnant women were assayed, all dilutions of the reference standard and test sera were made using QCMS as the diluent, and all of the assay tubes contained 500 μl serum. The tubes were swirled on a Vortex mixer after each addition of the various reagents. The tubes were then incubated for 24 hours at 4° C., after which 200 μl diluted second antobody solution at rabbit antigoat 1 gG serum (Research Products International, Elk Grove Village, IL; 1:10 dilution in RIA buffer) were added to each tube. The contents of the tubes were mixed, and the tubes were incubated at 4° C. for 24 hours and centrifuged at 4° C. at 1500×g for 30 min. After centrifugation, the supernates were aspirated, and the radioactivity in the precipitates was counted at 50% efficiency in a Bair Atomic Spectrometer (Model 530, Baird Atomic, Bedfor, Ma.). After correction for NSB, a dose-response curve was plotted as logit vs. log mass of PEP. Sample values were interpolated from the dose-response curve. Since the reference standard used in the RIA was not completely purified, values were expressed as units per ml serum or units per mg tissue cytosol or AF protein, 1 U being the response obtained in the dose-response curve with 1 ng reference standard. Sensitivity and reproducibility were determined by the method of Rodbard. The standard significance of the differences in the PEP concentrations was evaluated by multiple t test.

EXAMPLE 6

(Equilibrium type RIA of PEP in endometrium and AF samples)

Assays for quantitation of PEP in endometrial cytosols and AF samples were set up according to the protocol described above. A dose-response curve obtained by testing the various standards in the RIA buffer in quadruplicate is shown in FIG. 1. The curve was essentially linear between 10-500 ng, with the interassay coefficient of variation (CV) ranging from 2-13%. The sensitivity and reproducibility of the assay were evaluated in 10 experiments in which the various standards were tested in duplicates. In these experiments, the specific binding of the tracer to anti-PEP in the absence of non-radioactive PEP ($B_o$) was 63.3±2.7% (mean±SD) and the NSB (determined in the presence of an excess of nonradioactive PEP) was 4% or less. The lowest detectable amounts of PEP which were significantly different from zero (Calculated as B minus 2 SD) varied from 4-8 ng. For practical purposes, the lower and upper limits of sensitivity were arbitrarily set at 10 and 300 ng/assay tube, respectively. At these points, the interassay CVs werewere 4.9% and 12.6%, respectively (Table 1). In 10 assays, the slope of the curve was found to be 2.68±0.10, with a midrange level of 29.2±3.7 ng.

TABLE 1

Reproducibility of the dose-response curve assessed by interassay CV in 10 different assays

| Reference antigen (ng/assay tube) | Curve obtained in the absense of QCMS | | Curve obtained in the presence of QCMS | |
|---|---|---|---|---|
| | Binding of tracer (mean ± SD) | CV (%) | Binding of tracer (mean ± SD) | CV (%) |
| 0 | 100 | | 100 | |
| 10 | 80 ± 3.8 | 4.9 | 89 ± 1.8 | 2 |
| 20 | 64 ± 3.9 | 6.0 | 81 ± 3.3 | 4 |
| 50 | 34 ± 4.0 | 11.8 | 60 ± 3.8 | 6 |
| 100 | 17 ± 2.5 | 14.6 | 43 ± 4.3 | 10 |
| 200 | 9 ± 1.3 | 14.0 | 27 ± 3.3 | 12 |
| 300 | 6 ± 0.8 | 12.6 | 22 ± 2.9 | 13 |
| 500 | 4 ± 0.6 | 15.0 | 15 ± 1.5 | 10 |

For comparison of the samples of endometrial cytosols and AF with standards, dilutions of the QCDC and QCAF were made in the RIA buffer and analyzed along with the standards. Such analyses generated curves which were almost parallel to the standard curve (FIG. 1). Reproducibility was tested by assaying aliquots of QCDC and QCAF in ten different assays. The concentrations of PEP in QCDC and QCAF were found to be 125,000±1,387 and 99,600±855 U/ml sample, respectively, with interassay CVs of 11.1% and 8.6, respectively.

The RIA described herein is highly specific, since none of the known pregnancy proteins tested, including $\alpha_1$-antitrypsin, ceruloplasmin, transferrin hPRL, hCG, and uteroglobin interfered with the binding of the tracer PEP to anti-PEP, and [$^{125}$I]PEP did not react with antibodies to several of the known pregnancy proteins, including hPRL, hPL, PZP, SP$_1$, AFP, PAPPs, PAPP-A, PAPP-C, uteroglobin, transferrin, ceruloplasmin, and $\alpha_1$-antitrypsin. These results confirm previous findings that PEP is not related to several of the known pregnancy proteins, including uterglobin which is the most widely studied progestin-dependent uterine protein. The RIA is highly reproducible; since the interassay CVs for the slopes of the curves were quite small (<5%), and those for the values of the quality control samples never exceeded 14%. Those skilled in the art will be aware that the assay is much more sensitive than indicated by the data herein, since the reference antigen used to obtain standard curves was not completely purified. A further improvement in the assay sensitivity could be obtained by using nonequilibrium-type conditions. The high sensitivity of the assay (lower limit of detection, 4-20 ng) coupled with the ability of the assay to handle large sample aliquots (up to 500 μl) has permitted the measurement of small amounts of PEP in such tissues and body fluids as the proliferative phase endometria and pregnancy sera, in which PEP could not be detected or quantitated by other immunological methods, [Joshi et al, supra]. Based on the results of PEP analysis in the cyling endometria, PEP can be measured with confidence in as little as 50 mg proliferative and 10 mg midsecretory phase endometrium. Therefore, the RIA will be useful in the analysis of endometrial tissues which are obtained by biopsy techniques.

The results of PEP analysis in endometria at different developmental stages and in AF samples are incorporated in Table 2.

TABLE 2

PEP concentrations in endometrium and AF samples

| Specimen | Status of Specimen Donor | n | PEP conc. (U/mg soluble protein)" |
|---|---|---|---|
| Endometrium | Proliferative phase of the menstrual cycle | 10 | 60 ± 20 |
| Endometrium | Early secretory phase of the menstrual cycle | 10 | 140 ± 70 |
| Endometrium | Midsecretory phase of the menstrual cycle | 11 | 2,900 ± 730 |
| Uterine decidua | Early pregnancy (6-10 weeks) | 11 | 70,000 ± 19,000 |
| AF | Pregnancy weeks 14-18 | 10 | 13,660 ± 3,950 |
| AF | Pregnancy weeks 20-30 | 5 | 2,560 ± 1,330 |
| AF | Pregnancy weeks 36-42 | 10 | 930 ± 240 |

"All values are the mean ± SE. One unit corresponds to the response obtained by 1 ng reference antigen in the RIA.

Endometria from 31 nonpregnant women were classified by histological examination as being in the proliferative (n=10), early secretory (n=10), or midsecretory phase (n=11). None of the 31 tissues was in the late secretory phase. The concentration of PEP in the early secretory phase tissues was not significantly different from that in the proliferative phase tissue. However, the concentration in the midsecretory phase endometrium (mean±SE, 2900±730 U/mg cytosol protein) was significantly greater (P<0.01) than that in the proliferative phase tissue (60±20 U/mg cytosol protein) or in the early secretory phase tissue (140±70 U/mg cytosol protein). The concentration of PEP in the decidua of women in early pregnancy (70,000±19,000 U/mg cytosol protein) was significantly greater (P<0.01) than that in the midsecretory phase tissues of the nonpregnant women. Thus, the mean concentration of PEP in midsecretory phase endometria was forty-eight-fold higher than in proliferative phase endometria and the mean concentration in uterine decidua of early pregnancy (6-10 weeks, N=11) was about twenty-four-fold higher than in the mid-secretory phase endometria.

Twenty-five specimens of AF obtained during weeks 14-17 (n=10), weeks 20-30 (n=5), and weeks 36-42 (n=10) of pregnancy were assayed for PEP. The mean concentration was found to be significantly greater (P<1.01) in the samples obtained during weeks 14-18 (13,600×3,950 U/mg protein) than those collected during weeks 20-30 (2,560±1,330 U/mg protein) or weeks 36-42 (930±240 U/mg protein).

EXAMPLE 7

(Equilibrium-type RIA of PEP in non-pregnancy and pregnancy sera)

For the analysis of PEP in serum samples, the dose-response curve was obtained using quadruplicate aliquots of standards prepared in QCMS (500 μl/tube), as described above. This curve was also found to be linear between 10-500 ng (FIG. 2), with an intrassay CV ranging from 1-4%. In 10 assays using duplicate aliquots of the standards, the specific binding of the tracer in the absence of nonradioactive PEP($B_o$) was 55±2.6%, and the NSB was less than 4%. The lowest detectable amounts of PEP ranged from 8-20 ng. For practical purposes, the lower and upper sensitivity limits were arbitrarily set at 30 and 500 ng, respectively. At these points, the interassay CVs were 4% and 10%, respectively (Table 1). The slope of the curve was 2.44±0.13, with an interassay CV of 5%. Dilutions of QCPS in QCMS were tested for parallelism with the standard curve, and the curve obtained by the dilutions of QCPS was found to be almost parallel to the standard curve (FIG. 2). To study reproducibility, the same specimen of QCPS was assayed in ten different assays. The concentration of PEP in QCPS was found to be 1042±83 U/ml, with an interassay CV of 14.6%.

The results of the analysis of sera from 21 non-pregnant and from 53 pregnant women are incorporated in Table 3.

TABLE 3

PEP concentrations in sera of cycling and pregnant women

| Stage of menstrual cycle or pregnancy | n | PEP conc. (U/ml)" |
|---|---|---|
| Proliferative phase of the menstrual cycle | 10 | ND |
| Midsecretory phase of the menstrual cycle | 11 | ND |
| Pregnancy weeks 6-10 | 28 | 722 ± 90 |
| Pregnancy weeks 15-28 | 18 | 139 ± 29 |
| Pregnancy weeks 29-40 | 7 | 111 ± 28 |

"All values are the mean ± SE. One unit corresponds to the response obtained by 1 ng reference antigen in the RIA. ND, Not detected by RIA.

PEP could not be detected in any of the 10 samples of proliferative phase sera or 11 samples of the midsecretory phase sera. However, it was detected in all 53 pregnancy sera tested. The mean serum level of PEP during pregnancy weeks 5-12 (722±90 U/ml) was significantly higher (P<0.01) than that obtained during pregnancy weeks 15-28 (139±29 U/ml) or pregnancy weeks 29-40 (111±28 U/ml).

The relationship between serum PEP and serum human chorionic gonadotropin (hCG) levels during pregnancy was also studied.

Radioimmunoassay of hCG was carried out by the conventional method of Vaitukaitis et al [Ibid, 113: 751 (1972)] using rabbit anti-hCGβ serum (from NIAMDD and NICHHD) as the first antibody, goat anti-rabbit IgG serum (Research Products International) as the second antibody, hCG (CR-119 from NIAMDD and NICHHD) which was radioiodinated by the Chloramine-T method of Greenwood et al, supra, as the tracer and the second IS-hCG (World Health Organization) as the reference standard.

The statistical significance of the differences in the PEP of hCG concentrations in groups of sera was evaluated by multiple t test.

The results of the analysis of hCG and PEP in the serum samples obtained from 201 pregnant subjects are shown in Table 4.

TABLE 4

Serum concentration of PEP and hCG during uncomplicated pregnancy

| Stage of pregnancy (weeks) | N | PEP conc.[a] U/ml | hCG conc. IU/ml |
|---|---|---|---|
| 4–5 | 3 | 273 ± 44* | 4.5 ± 0.5* |
| 6–7 | 8 | 444 ± 82 | 24.8 ± 5.3 |
| 8–9 | 28 | 530 ± 49 | 35.5 ± 2.3 |
| 10–11 | 12 | 457 ± 99 | 29.5 ± 4.4 |
| 12–13 | 14 | 353 ± 68 | 29.1 ± 2.7 |
| 14–15 | 22 | 515 ± 76 | 22.3 ± 2.2 |
| 16–17 | 31 | 323 ± 42 | 14.3 ± 1.4 |
| 18–19 | 22 | 299 ± 27 | 10.9 ± 1.8 |
| 20–21 | 21 | 210 ± 21 | 8.8 ± 1.0 |
| 22–27 | 9 | 126 ± 19 | 10.9 ± 1.9 |
| 28–32 | 12 | 146 ± 33 | 9.0 ± 2.0 |
| 33–40 | 19 | 85 ± 14 | 11.2 ± 2.4 |

*All values are Mean ± SE
[a]One unit of PEP corresponds to the response obtained by 1 ng partially-purified PEP in the RIA.

In general, the patterns of changes throughout pregnancy in serum concentration of hCG and of PEP were markedly similar. The concentrations of both hCG and PEP increased markedly during the four-week interval between 4 and 7 weeks of pregnancy. After 8–9 weeks, the serum concentration of both hCG and PEP remained more or less constant until 14–15 weeks. Thereafter the concentrations of both hCG and PEP decreased progressively until 18–19 weeks and they remained at low levels during the remainder of pregnancy. No relationship between serum PEP and hCG concentration was observed in individual pregnant subjects.

EXAMPLE 8

The RIA method of the above examples was utilized to assay the amniotic fluid samples obtained from 97 women who underwent amniocentesis or termination of mid-trimester pregnancy. The results set forth in Table 5 reveal maximal levels of PEP in specimens obtained during pregnancy weeks 14–18.

TABLE 5

Concentration of PEP in amniotic fluid during pregnancy

| Stage of pregnancy (weeks) | No. of samples | Conc. of PEP (units/mg protein)[b] |
|---|---|---|
| 14–18 | 10 | 13,660 ± 3,950 |
| 20–30 | 5 | 2,560 ± 1,330 |
| 36–42 | 10 | 930 ± 240 |

The results set forth above (Examples 6–8) reveal striking changes in PEP concentrations in tissues and body fluids during various physiological states. The present results (Table 2) deomonstrate that the transformation of a proliferative phase human endometrium into a secretory phase tissue is associated with an increase of about 48-fold in the tissue concentration of PEP and that further transformation of the tissue into the decidua of pregnancy is accompanied by a further 24-fold increase in the tissue's antigen load. The main factor responsible for such a dramatic increase in tissue PEP synthesis is most likely the stimulus provided by progesterone, since previous studies have demonstrated a direct relationship between the endometrial concentration of PEP and serum progesterone levels in non-pregnant and pregnant women. Progesterone is implicated in the endometrial sensitization of stromal cells and their decidualization and also in the induction of secretory changes within the endometrial glands. Further recent studies demonstrate that PEP is localized exclusively in the glandular and surface epithelia [Mizurkiewicz et al, J. Clin. Endocrinal. Metab. (1981)] and other studies have strongly suggested that PEP is most likely secreted and transported to the amniotic sac [Joshi et al, J. Reprod. Fertil. 59: 275 (1980)]. The present results on AF (Table 5) confirm our earlier findings that the PEP level in AF declines rapidly after 18–20 weeks of pregnancy. This decline may be due to the onset of degenerative changes within the endometrial glands, impairment in the mechanism of transplacental transport from the decidua to the AF, or removal from the AF by degradation. Although the chemical nature of immunoreactive PEP in the endometrial tissue and AF has not been fully determined, the observed parallelism in the slopes obtained by dilutions of QCDS or QCAF and reference standard noted in this study and the findings of our previous study clearly indicated that the PEP of AF origin is biochemically similar to that of decidual origin.

The most significant finding of the study on pregnant women is the rapid increase in serum concentration of PEP that was noted by 8–9 weeks of pregnancy (Table 4). This period corresponds to 6–7 weeks post-ovulation, and the concentration of PEP in serum at this time (530±49 units per ml, Table 4) is about 20-fold higher than the peak concentration of PEP (26.9×4.3 units per ml) encountered in the serum of cycling women. Furthermore, the serum concentration of PEP which we observed during weeks 4–5 of pregnancy or weeks 2–3 post-ovulation (273±44 units/ml, Table 4) is about 10-fold higher than that encountered in the comparable two weeks post-ovulation (late luteal phase) in a non-pregnant, cycling woman (26.9±4.3 units/ml). The endometrium is the major source of PEP in pregnancy as indicated in the results (Table 2) of the above examples in that the concentration of PEP is more than 1000-fold higher in the decidua of early pregnancy (6–10 weeks) than in the pre-ovulatory, proliferative endometrium of non-pregnant women. Furthermore, PEP is readily detected (by Ouchterlony's immunodiffusion technique) in the cytosols of the decidual tissue but not of the trophoblasts of early pregnancy [Joshi et al, J. Reprod. Fertil. 60: 317 (1980)]. These observations, and the results of the above examples that an increase in serum PEP concentration during early pregnancy is accompanied by a similar increase in hCG concentration, strongly suggest an interdependency of endometrial and trophoblastic function. It is most likely that the increase observed in serum PEP concentration during early pregnancy (8–9 weeks) is due to hCG stimulated secretion of progesterone by the CL.

Since PEP is a secretory product of the endometrial glands, the decline in serum concentration of PEP which occurred after 14–15 weeks be due to the onset of degenerative changes within these structure. Apparently this tissue degeneration continues in the face of increasing progesterone levels since it has been observed that serum progesterone levels continue to rise until about 26 weeks of pregnancy and they remain high until parturition [Johannson, Acta. Endocrinol. 61: 607 (1969)].

It has been shown that 3–10% of infertile women have defective CL function [Radwanska, E., and Dwyer, G. I. M., J. Obstet. Gynecol. (Br. Comm.) 81: 107 (1974); Wemtz, A. C., Clin. Obstet. Gynecol. 22: 169 (1979)]. This percentage is much higher (35–50%)

in women with histories of habitual abortions and in patients in whom ovulation is induced with clomiphene or human menopausal gonadotrophin [Ross, G. T., Cargille, C. M., Lipsett, M. B., Rayford, P. L., Marshall, J. R., Strott, C. A., and Rodbard, D., Rec. Prog. Horm. Res. 26: 1 (1970)]. In this connection, it is presumed although not proven, that a CL which is defective during the menstrual cycle is also defective in early pregnancy. This defect results in an inadequate endometrial maturation and, consequently, failure of implantation. Although the methods for the diagnosis of CL defects have been extensively studied, very little is understood about the effects of the defective CL on the endometrial maturation during early pregnancy. Basic studies on laboratory animals have clearly demonstrated that the development of the endometrium during early pregnancy is critically dependent on the sequential action of estrogen (E) and progesterone (F) and that the amounts and ratio of the two hormones are important factors in the control of endometrial receptivity for the balstocyst [Ross, G. T., Cargille, C. M., Lipsett, M. B., Rayford, P. L., Marshall, J. R., Stott, C. A., and Rodbard, D., Rec. Prog. Horm. Res. 26: 1 (1970); Black, W. P., Martin, B. T., and Whyte, W. G., J. Obstet. Gynecol. (Br. Comm.) 79: 363 (1972); Mester, J., Martel, D., and Psychoyos, A., Nature, 250: 776 (1974)]. Furthermore, it has been shown that the magnitude of the hormonal response within the target issue (i.e., the endometrium) is dependent, to a large extent, on the availability of receptors for estrogen (E) and progesterone (P) [Mester, J., Martel, D., and Psychoyos, A., Nature, 250: 776 (1974)]. Also it has been shown that E and P control the concentration of their own receptors within the target tissue [Tseng, L., and Gurpide, E., J. Clin. Endocr. Metab. 41: 402 (1975); Bayard, F., Damilano, S., Robel, P., and Baulieu, E. E., J. Clin. Endocr. Metab. 46: 635 (1978); and Haukkamaa, M., Luukkainen, T. J., Steroid Biochem. 5: 447 (1976)]. Therefore, it is to be expected that a defective CL of the conception cycle or early pregnancy and associated suboptimal levels and ratios of estrogen and progesterone in blood will result in abnormal steroid hormone receptor levels in the endometrium and consequently altered endometrial function. A recent study by Gautray et al [Gautray, J. P., DeBrux, J., Tajchner, G., Robel, P. and Mouren, M., Fertil. Steril. 35: 296 (1981)] demonstrates that the cytosolic estrogen receptor and nuclear progesterone receptor concentrations in the endometrium associated with CL deficiency are significantly lower than those in the normal late secretory phase. Technical and ethical issues preclude the measurement of steroid hormone receptors in human endometrial during pregnancy. However, a blood-borne factor, such as PEP, which is actively synthesized within the endometrium and which is hormone-elicited is a more suitable marker with which to monitor endometrial function in women whose pregnancy may be threatened by defective CL function or by toxic agents. The utility of serum PEP may be further extended by simultaneous measurements of serum hCG (a marker of placental function). This information will provide important clues about the inter-relationship or interdependence of endometrial, placental and fetal functions in normal and abnormal pregnancies.

Finally, the magnitude of changes seen in the present study in serum PEP levels during early pregnancy (Table 4) suggests that PEP determinations in serial serum samples of early pregnancy may offer a sensitive, quantitative and non-invasive means of monitoring threatened pregnancies. Also, it is quite conceivable that the serum PEP measurement may be utilized to diagnose early pregnancy, and perhaps with greater confidence than is possible by serum hCG measurements.

EXAMPLE 9

(Non-equilibrium type RIA of PEP in sera of cycling women)

The following is an example of a non-equilibrium type RIA method of the present invention.

The "equilibrium-type" RIA of the above examples was used to quantitate PEP in the sera of pregnant women. However, the assay was not sufficiently sensitive to detect PEP in the sera of cycling women. To improve the sensitivity of the procedure, the assay was carried out under non-equilibrium, rather than equilibrium, conditions (using the same reagents as those determined for the equilibrium-type RIA) as follows: The reagents were added to disposable glass tubes in the following order, 100–500 µl test serum sample in tubes for unknowns, 100 µl reference antigen solution containing 2.5–250 ng PEP in the tubes for dose-response curve, 100 µl reference antigen solution containing excess (3.5 µg) PEP in tubes for measuring nonspecific binding of the tracer to the first antibody (or trapping of the tracer during the precipitation of antigen-1st antibody complex) quality control male serum (QCMS) to all tubes in a volume sufficient to adjust final serum volume to 500 µl per tube, and 100 µl first antibody solution (IgG fraction, 27 mg/ml, of the absorbed goat anti-PEP serum, diluted 1:1250 in 10 mM phosphate—0.154 M NaCl—10 mM EDTA—).1% (w/v) bovine serum albumin—0.1% (w/v) NaN$_3$, pH 7.6 supplemented with 0.25% (v/v) normal goat serum. The tubes were swirled on a vortex mixer after each addition of the various reagents. The tubes were then incubated for approximately 72 hours at 4° C. after which 100 µl tracer solution (approximately 40,000 cpm of [$^{125}$I]PEP were added to each tube. The tubes were reincubated for about 8 hours at 40° C. after which 200 µl of the 2nd antibody solution (which was diluted 1:10 in the RIA buffer) were added to each tube. After mixing the contents, the tubes were further incubated for about 24 hours at 4° C. and centrifugated at 4° C. at 1500 g for 30 min. After centrifugation, the supernates were aspirated and the radioactivity in the precipitates was counted at about 59% efficiency in a Baird Atomic Spectrometer (Model 530, Baird-Atomic, Bedford, MA). After correction for non-specific binding, a dose-response curve was plotted as logit vs. log mass of PEP. Sample values were interpolated from the dose-response curve. Since the reference standard used in the RIA was not completely purified, values in test samples (both pregnancy and non-pregnancy sera) were expressed as units per ml serum, one unit being the response obtained in the dose-response curve with 1 ng reference standard. The assay parameters (sensitivity and reproducibility) of the non-equilibrium PEP RIA were determined by the method of Rodbard [Clin. Chem. 21: 1255 (1974)].

Characteristics of the Non-Equlibrium PEP RIA

A preliminary study of 10 different assays was undertaken to determine characteristics of the modified RIA. The specific binding of the tracer to anti-PEP in the absence of non-radioactive PEP (B$_o$) was 40.7±2.6%

(mean±SD) with an interassay coefficient of variation (CV) of 6.3% and non-specific binding, determined in presence of an excess of non-radioactive PEP, was 2.6±0.2% with an interassay CV of 7.2%.

A dose-response curve obtained by testing the various standards in the RIA buffer in quadruplicate is shown in FIG. 3 and the intraassay and interassay CVs for responses obtained at each dose level are incorporated in Table 6.

The curve was essentially linear between 2.5 and 250 ng with an intrassay CV ranging from 3.2 to 5.7%. The slope of the curve was 2.2±0.1 with a mid range level of 16.0±1.9 ng (FIG. 3). Although the lower limit of sensitivity of the assay (calculated as $B_o$ minus 2 SD) was 1.5±0.5 ng, the interassay CV at this level was quite high (34.2%). For practical purposes the lower and upper limits of sensitivity were arbitrarily set at 2.5 and 250 ng per assay tube, respectively. At these levels, the interassay CVs were 2.8% and 3.8%, respectively (Table 6). The assay was highly reproducible since the interassay CV for the slopes of 10 dose-response curves was less than 5% and the interassay CV for the concentration of PEP in the quality control serum in 10 assays was less than 12%.

TABLE 6

Accuracy and reproducibility of the dose-response curve for PEP

| | Results of a single assay | | Results of 10 different assays | |
|---|---|---|---|---|
| (ng/assay tube) | Binding of tracer (%) | Intra assay CV (%) | Binding of tracer (%) | Inter assay CV (%) |
| 0 | 100 | — | 100 | — |
| 2.5 | 85 ± 2.8[a] | 3.3 | 86 ± 2.4[a] | 2.8 |
| 5.0 | 72 ± 4.1 | 5.7 | 76 ± 4.0 | 5.2 |
| 10 | 58 ± 2.9 | 4.9 | 59 ± 1.1 | 1.9 |
| 25 | 32 ± 1.5 | 4.8 | 34 ± 2.8 | 8.2 |
| 50 | 21 ± 1.1 | 5.3 | 22 ± 1.3 | 5.7 |
| 100 | 13 ± 0.4 | 3.2 | 14 ± 0.7 | 4.8 |
| 250 | 9 ± 0.4 | 4.1 | 9 ± 0.4 | 3.8 |

[a]Values are Mean ± SD.

Analysis of Serum P and PEP in Cycling Women

A total of 74 serum samples were obtained from the fourteen women who were enrolled in the study. For the sake of convenience, the sera obtained during cycle days 13–15, 16–19, 20–23 and 24–27 were respectively designated as periovulatory, early luteal, mid-luteal and late luteal phase samples. Analysis showed that PEP was present in the sera of 12 of the 14 subjects. The analyses of serum PEP and P in these 12 PEP positive subjects are summarized in Table 7.

TABLE 7

P and PEP concentrations in the serum samples of subjects 1 through 12

| Status of serum donor | Number of serum samples | P conc. (ng/ml) | PEP conc. (U/ml) |
|---|---|---|---|
| Perovulatory phase (cycle days 13–15) | 12 | 2.1 ± 0.6[a] | 2.2 ± 1.0[a] |
| Early luteal phase (cycle days 16–19) | 18 | 10.8 ± 1.2 | 1.8 ± 1.1 |
| Mid-luteal phase (cycle days 20–23) | 17 | 17.8 ± 1.7 | 4.4 ± 1.0 |
| Late luteal phase (cycle days 24–27) | 16 | 8.7 ± 1.8 | 26.9 ± 4.3 |

[a]All values are the Mean ± SE. One unit of PEP corresponds to the response obtained by 1 ng partially purified PEP in the RIA.

As expected, the mean level of P was significantly higher in the mid-lueal phase sera (17.8±1.7 ng per ml) than in sera obtained in the periovulatory, early luteal or late luteal phase (P<1.01). In contrast, the mean level of PEP was relatively low (less than 5 units per ml) during the periovulatory, early luteal or mid-luteal phase sera but it was markedly high (30±4 units per ml) in the late luteal phase sera.

Analysis of the serial samples of serum obtained from 14 women revealed three different patterns of changes in serum P and PEP which are shown in FIG. 4, [solid bar indicates period of menstruation], including the typical and two atypical patterns. The pattern shown for subject No. 12 occurred most frequently, appearing in the twelve of the fourteen women studied, and is probably typical for a normal menstrual cycle. It is characterized by a mid-luteal phase increase in serum P level followed by a late luteal phase rise in serum PEP. In all 12 of the subjects in whom this typical pattern was seen, the mid-luteal phase P levels exceed 8 ng per ml. An atypical pattern, obtained in subject No. 13, was clearly indicative of corpus luteum inadequacy, since the mid-luteal phase serum P level was markedly low (5.8 ng/ml as compared to 17.8 ng/ml encountered in normal subjects, Table 7). No PEP was detected in any of the serum samples from this subject. A second atypical pattern seen in subject No. 14 showed the amount and duration of P secretion by the Cl that were quite comparable to those in normal subjects (Table 7), yet no PEP was detected in any of the serum samples.

There is achieved at least a 10-fold increase in the sensitivity of RIA for PEP without the loss of reproducibility by performing the assay under non-equilibrium conditions, rather than under the equilibrium conditions described above. Utilizing this modified RIA technique, it is demonstrated that, in the majority of cycling women (12 of our 14 subjects) with adequate luteal function, serum PEP levels are significantly increased during the late luteal phase (Table 7, FIG. 4). This increase is most likely due to progestin-induced stimulation of the synthesis and secretion of PEP by the endometrium, since we have previously shown that the concentration of PEP in the cycling endometrium increases progressively from the proliferative phase through midsecretory phase and it continues to increase during early pregnancy. However, it is not altogether clear as to why serum PEP levels should peak during the late luteal phase at a time when the serum P levels have declined from the peak attained during mid-luteal phase. According to the current concepts of steroid-hormone action, steroids bind to their specific receptors in the cytoplasm of the target cells. The steroid-receptor complexes are then translocated to the nucleus where they interact with the nuclear chromatin to stimulate synthesis of specific messenger RNAs. Messenger RNAs (mRNAs) in turn direct the synthesis of spectific steroid-dependent proteins. The time required for nuclear steroid hormone receptors to elicit mRNA synthesis and the stability of the mRNAs determine, to a large extent, the rapidity of response of the target cell to hormones and the duration of the response. Bayard et al [J. Clin. Endocr. Metab. 46: 335 (1978)] have shown that in the endometria of cycling women there is a significant decrease in the concentration of progesterone receptors (PR) in the cytoplasm and a concomitant increase in the PR concentration in the nucleus during the early luteal phase. Furthermore, they found that PR in the cytoplasm and nucleus are at its lowest level during the late luteal phase. That chronology of events involving PR, and the sequence of changes in the endometrial PEP concentrations in cycling women reported in the above examples and in the serum PEP levels as shown in Table 8, FIG. 4, suggest the following sequence. The increase in PR concentration in the endometrium during the early luteal phase triggers the synthesis of long-lived messenger RNAs which in turn stimulate PEP synthesis during the mid-luteal and late luteal phase. Furthermore, the observed peak in the late luteal serum PEP level indicates that the PEP continues to accumulate in the endometrial tissue and blood, perhaps due to its slow turnover rate. An analogous situation has been reported with respect to changes in PR concentrations, mRNA activity and synthesis of uteroglobin (which is a progestin-dependent rabbit uterine protein) in the endometria of pregnant rabbits. Young et al [Mol. Cell. Endocr. 22: 105 (1981)] observed that in pregnant rabbits, endometrial nuclear concentration of PR rose on day 2 of pregnancy and declined thereafter whereas the concentration of uteroglobin mRNA continued to increase until day 4. Mayol and Longnecker [Endocrinology 95: 1534 (1974)] found that the total amount of uteroglobin in uterine secretions begins to rise steadily from day 3 until day 6. Whatever the mechanisms of the late luteal phase increase in serum PEP levels in women may be, it is apparent that a late luteal phase serum level of PEP in cycling women reflects the cumulative effect of progesterone on the human endometrium.

There is now sufficient evidence of the requirement for progesterone as well as estrogen in the development of endometrial receptivity for the primate fertilized ovum [Thau, R. B. and Sundaram, K., Fertil. Steril. 33: 317 (1980)]. Also, it is clearly evident that abnormalities in the amount and duration of progesterone secretion during the menstrual period are associated with infertility [Horta, J. L. H., Fernandez, J. G., DeSoro, L. B., Cortez-Gallegos, V., Obstet. Gynecol. 49: 705 (1977)]. Serveral parameters, including basal body temperatures (BBTs), vaginal cytology, changes in cervical mucus, histologic dating of the endometrium and blood progesterone (or urinary pregnandiol), are now being used to evaluate CL function in infertile women. However, it is becoming increasingly apparent that none of the above parameters, when used alone, provide an accurate assessment of CL function. In a study reported by Radwanska and Dwyer [Radwanska, E., and Dwyer, G. I. M., J. Obstet. Gynecol. (Br. Comm.) 81: 107 (1974)], BBT charts were monophasic (atypical) in 12% of normal ovulatory cycles (as indicated by blood progesterone levels), and biphasic (typical) in 72% of the cycles which were deficient in progesterone. Thus, BBT charts provide only suggestive evidence of a CL defect. Blood progesterone levels provide a quantitative measure of CL function. Jones et al [Jones, G. S., Aksel, S. and Wentz, A. C., Obstet. Gynecol. 44: 26 (1974)] studied blood progesterone levels throughout the menstrual cycle in 10 patients with histologically proven luteal phase defects and 28 patients with normal CL function and found that the areas under the curves were significantly different for the two groups. However, due to wide variation in blood progesterone levels in individual patients, it is impossible to establish CL defect by determination of a single progesterone level. By far the most valid method for detecting CL defects is the histologic examination (dating) of an endometrial biospy specimen which is obtained on day 21, 22 or 23 (representing the period of maximal CL activity) or on cycle day 26 (representing the cumulative influence of progesterone during the entire cycle). Dating of the endometrium is correlated with the apparent day of ovulation and with the day of the onset of the next menstrual cycle. Biopsies are evaluated for at least two cycles since the incidence of the occurrence of out-of-phase endometrium in normal cycles is quite high (about 20%) [March, C. M. in "Reproductive Endocrinology, Infertility and Contraception". Ed. D. R. Mishell and V. Davajan. F. A. Davis Company, Philadelphia, 1979 pp. 469–476]. However, the method of endometrial dating is, at best, semi-quantitative and traumatic. Therefore, the PEP-RIA method of the present invention is far superior to previous methods. Since PEP levels in normally cycling women rise markedly and reach a peak during the late luteal phase, it is conceivable that a single or multiple serum PEP determination at the end of the cycle (day 26, 27 or 28) coupled with a BBT chart for each of the two consecutive cycles may provide a simple, non-invasive and a quantitative means to assess CL function in infertile women.

EXAMPLE 10

(PEP as a marker to predict responses of endometrial tumors to progestin therapy)

Progestin therapy alone has been used in the management of atypical endometrial hyperplasias or carcinoma of the endometrium in situ [Pelligrini, A., Massidda, B., Mascia, V., Lippi, M. G., Ionta, M. T., Muggiano, A., and E. Carboni-Boi, in "Role of Medroxyprogesterone in Endocrine-related Tumors". Iscobelli, S., and DiMarco, A., Eds. Raven Press, 1980, pp. 29–51; Nilson, P. A., and Kolstad, P. in "Endometrial Cancer". Brush, M. G., Taylor, R. W., and Williams, D. C., Eds. William Heinemann Medical Books, London, 1973; Steiner, G. J., Kistner, R. W. and Craig, J. M. "Metabolism 14: 356, 1965]. Progestins have also been successfully employed by adjunct therapy in the treatment of endometrial cancer [Bonte, J., Drochmans, A. and Ide, P., in "Second International Congress on Hormonal Steroids". Excerpta Medica International Congress Series No. 111; 307, 1966]. The search for methods of selecting, in advance of hormone therapy, those cancer patients who might respond to progestin has met with limited success. The most widely explored method of the selection assumes that the presence of a cytoplasmic (or nuclear) PR in normal or neoplastic tissue is a necessary requirement for the response of those tissues to progestin. The selection method involves the measurement of tumor ER and/or PE (which are known to be regulated by progestins) before and after in vivo or in vitro challege with a progestin. Since the synthesis of PR is stimulated by estrogen ["Hormones, Receptors and Breast Cancer", McGuire, W. L., Ed. Raven Press, New York, 1978], it is reasonable to further assume that those tumors containing PR alone or E receptors (ER) plus PR are more likely to respond to progestins than tumors without these receptors. Recent reports [Hunter, R. E., Longscope, C. and Jordan, V. C., Gynecol-Oncology 10: 152 (1980); Anderson, D. G., Am. J. Obstet. Gynecol. 92: 87 (1965); Kennedy, B. J., Surg. Gynecol. Obstet. 127: 103 (1968); Reifenstein, E. C., Cancer 27: 485 (1971); and Kelly, R. M. and Baker, W. H., Cancer Res. 25: 1190 (1965)] indicate that about 70% of the endometrial adenocarcinomas contain estrogen receptors and 52% of tumors contain both estrogen and progesterone receptors. However, only 30–35% of the recurrent and/or metastatic endometrial cancer patients respond to progestin therapy. In other words, 50–70% or so of the patients do not respond to progestin therapy in spite of the presence of progestin receptor in the tumors. An analogous situation is encountered in studies on human breast tumors, 40% of which do not respond to hormone therapy in spite of the presence of estrogen receptor in tumor [Lippman, M. E. and Allegra, J. C., New Engl. J. Med. 29: 930 (1978); and McGuire, W. L. and Horowitz, K. B. in "Hormones, Receptors and Breast Cancer", Ed. McGuire, W. L., Raven Press, New York (1978)]. It is believed that many steroid hormone receptors in tumors are nonfunctional, i.e., the binding of hormones to their respective receptors do not elicit a biologic response and therefore, the receptors, when studied alone, cannot provide a reliable indication of the tumor's responsiveness to hormones. Based on studies of estrogen receptors or progestin receptors in endometrial adenocarcinomas, Hunter et al [Hunter, R. E., Longscope, C. and Jordan, V. C., Gynecol-Oncology 10: 152 (1980)], have concluded that at the present time the only practical value of ER or PR determination on the primary tumor is in planning therapy for management of metastatic disease that might subsequently occur. The biochemical marker having the greatest utility in predicting responses of endometrial cancers to progestin therapy must signal an endometrial response to "progestin-action-in-progress". PEP satisfies the above basic requirement and therefore it can serve as a marker for the selection of patients who are likely to respond to progestin therapy. Thus, it has been determined that two of three endometrial tumors containing PR responded to in vivo progestin (Megace, Mead Johnson) with increased tissue synthesis of PEP and in one of these two patients, the exogenous progestin caused a marked increase in blood PEP level.

The human endometrium synthesizes PEP, a progestin-dependent protein. This protein has been well characterized and it can be detected in the peripheral blood. The RIA methods of the present invention will enable those skilled in the art to quantitate PEP in tissues and body fluids and to localize it in specific cell types. This invention will now permit the detection of early pregnancy, exploration of the biologic role of the protein in pregnancy to diagnose corpus luteum defects, and to determine the clinical utility of this protein as a marker of endometrial responsiveness to endogenous and exogenous progestins. As will be apparent to those skilled in the art, these methods are must more sensitive than the previously published method of RIEP. To our knowledge, no one else has developed such RIA methods for PEP, although Sutcliffe et al [Sutcliffe, R. G., Bolton, A. E., Sharp, F., Micholson, L. V. B. and Mackinnon, R. J., Reprod. Fertil. 58: 435 (1980)] have purified and radioiodinated a protein which is similar to PEP. However, they have not yet developed a radioimmunoassay for the protein nor have they studied the clinical utility of the protein. The RIAs of the present invention have the following specific potential clinical applications:

1. To diagnose corpus luteum (CL) defects in infertile women.
2. To diagnose endometrial insensitivity to endogenous or exogenous progestins in infertile women or in pregnant women who are receiving progestin treatment for CL defects.
3. To diagnose early pregnancy (pregnancy test).
4. To diagnose CL defects in pregnant women with histories of abortions.
5. To select in advance endometrial cancer patients who may benefit from progestin therapy.
6. To determine the extent of ectopic endometrial growth in endometriosis patients.

I claim:

1. A radioimmunoassay method for the quantitative determination of PEP in a body fluid comprising:
   (a) partially purifying PEP chromatographically;
   (b) radioisotopically labelling said partially purified PEP and further purifying it chromatographically;
   (c) preparing an antibody specific against PEP using said partially purified PEP as an antigen;
   (d) admixing a sample of the body fluid suspected of containing PEP with radioisotope labeled PEP and said antibody against PEP;
   (e) incubating said mixture for a time sufficient to allow unlabeled PEP and radioisotope labeled PEP to competitively bind on said antibody against PEP;
   (f) separating from said mixture antibody against PEP to which is bound unlabeled PEP and radioisotope labeled PEP;
   (g) measuring the radioactivity of the separated antibody against PEP to which is bound unlabeled PEP and radioisotope labeled PEP; measuring the radioactivity of the mixture from which the antibody against PEP to which is bound unlabeled PEP and radioisotope labeled PEP was separated; or measuring the radioactivity of both the antibody against PEP to which is bound unlabeled PEP and radioisotope labeled PEP and the mixture from which it was separated to determine the content of PEP in said body fluid.

2. The method of claim 1 wherein said body fluid is serum.

3. The method of claim 1 wherein said body fluid is amniotic fluid.

4. The method of claim 1 wherein said body fluid is endometrial fluid.

5. The method of claim 1 wherein said radioisotope is selected from the group consisting of $^{125}I$, and $^{131}I$.

6. The method of claim 1 wherein said radioisotope is $^{125}I$.

7. The method of claim 1 wherein said antibody is derived from goat.

8. The method of claim 1 wherein said antibody containing bound unlabeled PEP and radioisotope-labeled PEP is separated from said mixture by precipitation of said bound antibody and removal of said precipitate from said mixture.

9. The method of claim 8 wherein said precipitate is effected by inclusion in said mixture of body fluid sample, unlabeled PEP, radioisotope labeled PEP and a second antibody which is an antibody against said first antibody but is not an antibody against PEP, said antibody forming a precipitate upon binding with said first antibody to which is bound unlabeled and labeled PEP.

10. The method of claim 9 wherein said second antibody is derived from an animal species other than that from which the first antibody is derived.

11. The method of claim 10 wherein said first antibody is goat antibody and said second antibody is rabbit anti-goat antibody.

12. The method of claim 1 wherein the radioactivity of the separated antibody against PEP to which is bound unlabeled and radioisotope labeled PEP is measured to determine the content of PEP in said body fluid sample.

13. The method of claim 1 wherein the content of PEP in said body fluid sample is determined by comparison of said measured radioactivity with a dose-response curve plotted from the results of the radioimmunoassay method of claim 1, employing as body fluid samples, aqueous solutions containing known amounts of PEP, partially purified according to the method of claim 1.

14. A composition of matter adapted for use in a radioimmunoassay method for the quantitative determination of PEP in a body fluid comprising PEP labeled with a radioactive isotope, prepared according to the method of claim 1.

15. The composition of claim 14 wherein said radioactive isotope is selected from the group consisting of $^{125}I$ and $^{131}I$.

16. The composition of claim 14 wherein said radioisotope is $^{125}I$.

17. The composition of claim 14 wherein said radioisotope is linked to said PEP through the tyrosyl moiety thereof.

18. A composition in kit form adapted for radioimmunoassay of a body fluid to determine the PEP content thereof comprising, in separate packages:
 (1) a radioisotope-labeled PEP and
 (2) an antibody against PEP, each prepared according to the method of claim 1.

19. The composition in kit form of claim 18 additionally containing, in separately packaged form:
 (3) a second antibody against said antibody against PEP of claim 18 and
 (4) a series of unlabeled PEP solutions, partially purified according to the method of claim 1, for use as reference standards in said radioimmunoassay.

20. The composition of claim 18 wherein said radioisotope is selected from the group consisting of $^{125}I$ and $^{131}I$.

21. The composition of claim 18 wherein said radioisotope is $^{125}I$.

22. The composition of claim 18 wherein said antibody against PEP is derived from goat.

23. The composition of claim 19 wherein said antibody against PEP is derived from goat and said second antibody against said antibody against PEP is derived from rabbit.

24. In a method for diagnosing conditions of the human body which affect the production or maintenance of the level of progesterone in the endometrium, the improvement comprising determining the content of PEP in a body fluid of the human by a radioimmunoassay comprising:
 (a) partially purifying PEP chromatographically;
 (b) radioisotopically labeling said partially purified PEP and further purifying it chromatographically;
 (c) preparing an antibody specific against PEP using said partially purified PEP as an antigen;
 (d) admixing a sample of the body fluid, radioisotope labeled PEP and said antibody against PEP;
 (e) incubating said mixture for a time sufficient to allow unlabeled PEP and radioisotope labeled PEP to competitively bind said antibody against PEP;
 (f) separating from said mixture antibody against PEP to which is bound unlabeled PEP and radioisotope labeled PEP; and
 (g) measuring the radioactivity of the separated antibody against PEP to which is bound unlabeled PEP and radioisotope labeled PEP measuring the radioactivity of the mixture from which said antibody against PEP was separated, or measuring the radioactivity of both the separated antibody against PEP to which is bound unlabeled PEP and radioisotope labeled PEP and the mixture from which it was separated to determine the content of PEP in said body fluid;
 and further ascertaining therefrom the level of progesterone in the endometrium.

25. The method of claim 24 wherein said body fluid is serum.

26. The method of claim 24 wherein said body fluid is amniotic fluid.

27. The method of claim 24 wherein said body fluid is endometrial fluid.

28. The method of claim 24 wherein said radioisotope is selected from the group consisting of $^{125}I$ and $^{131}I$.

29. The method of claim 24 wherein said radioisotope is $^{125}I$.

30. The method of claim 24 wherein said antibody is derived from goat.

31. The method of claim 24 wherein said antibody against PEP to which is bound unlabeled PEP and radioisotope labeled PEP is separated from said mixture by precipitation of said bound antibody and removal of said precipitate from said mixture.

32. The method of claim 31 wherein said precipitation is effected by inclusion in said mixture of body fluid sample, unlabeled PEP and radioisotope-labeled PEP a second antibody which is an antibody against said first antibody but is not an antibody against PEP, said second antibody forming a precipitate upon binding with said first antibody to which is bound unlabeled- and labeled-PEP.

33. The method of claim 32 wherein said second antibody is derived from an animal species other than that from which the first antibody is derived.

34. The method of claim 33 wherein said first antibody is goat antibody and said second antibody is rabbit anti-goat antibody.

35. The method of claim 24 wherein the radioactivity of the separated antibody containing bound unlabeled- and radioisotope-labeled-PEP is measured to determine the content of PEP in said body fluid sample.

36. The method of claim 24 wherein the content of PEP in said body fluid is determined by comparison of said measured radioactivity with a dose response curve plotted from the results of the radioimmunoassay methods of claim 25 employing as body fluid samples, aqueous solution containing known amounts of said partially purified PEP.

37. The method of claim 1 wherein the assay is carried out under non-equilibrium conditions.

* * * * *